US00PP37276P2

(12) United States Plant Patent
Moucheboeuf

(10) Patent No.: US PP37,276 P2
(45) Date of Patent: Feb. 17, 2026

(54) ***DIANTHUS* PLANT NAMED 'KLEDA26818'**

(50) Latin Name: ***Dianthus* x *allwoodii hort***
Varietal Denomination: KLEDA26818

(71) Applicant: KLEMM + SOHN GMBH & CO. KG, Stuttgart (DE)

(72) Inventor: Laetitia Moucheboeuf, Exeter (GB)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 19/276,867

(22) Filed: Jul. 22, 2025

(51) Int. Cl.
*A01H 5/02* (2018.01)
*A01H 6/30* (2018.01)

(52) U.S. Cl.
USPC ..... Plt./272
CPC ..... *A01H 6/305* (2018.05); *A01H 5/02* (2013.01)

(58) Field of Classification Search
USPC ..... Plt./263.1, 272
See application file for complete search history.

(56) References Cited

U.S. PATENT DOCUMENTS

PP32,444 P2 * 11/2020 Klemm ..... A01H 6/305
Plt./277

* cited by examiner

*Primary Examiner* — Karen M Redden
(74) *Attorney, Agent, or Firm* — Weatherly IP Solutions, LLC; John E. Pritchard; James Weatherly

(57) ABSTRACT

A new *Dianthus* plant designated 'KLEDA26818' particularly distinguished by pink flowers with a maculated pattern; and an upright and round plant form, is disclosed.

1 Drawing Sheet

Genus and species: *Dianthus x allwoodii hort.*
Variety denomination: 'KLEDA26818'.

BACKGROUND OF THE NEW PLANT

The present invention comprises a new and distinct variety of *Dianthus*, botanically known as *Dianthus* x *allwoodii* hort and hereinafter referred to by the variety name 'KLEDA26818'. 'KLEDA26818' originated from an open cross pollination from the proprietary female parent 'DSA-2024-3W503' (unpatented) and an unknown male parent during 2015 between May and August in Ashcombe, United Kingdom.

Seeds from the cross were obtained. The seeds were sown and plants grown for evaluation. A single plant was selected during June 2016 and subsequently named 'KLEDA26818'. During September 2016 'KLEDA26818' was first vegetatively propagated by stem cuttings in Ashcombe, UK. 'KLEDA26818' was found to reproduce true to type in successive generations of asexual propagation in Ashcombe, United Kingdom.

SUMMARY

The following are the most outstanding and distinguishing characteristics of 'KLEDA26818' when grown under normal horticultural practices in Stuttgart, Germany.

1. Pink flowers with a maculated pattern; and
2. An upright and round plant form.

DESCRIPTION OF THE PHOTOGRAPHS

This new *Dianthus* plant is illustrated by the accompanying photographs taken in October 2024 of a 14-week old whole plant of 'KLEDA26818' that was grown indoors in Stuttgart, Germany. The photographs show the foliage, buds, and flowers and the colors shown are as true as can be reasonably obtained by conventional photographic procedures.

DESCRIPTION

The following detailed descriptions set forth the distinctive characteristics of 'KLEDA26818'. The data which define these characteristics were collected from asexual reproductions carried out in Stuttgart, Germany. Data was collected in April 2025 from a 6-month-old plant that was grown in a plastic greenhouse over the winter in low temperature conditions in Stuttgart, Germany. Color references are to The R.H.S. Colour Chart of The Royal Horticultural Society of London (R.H.S.), 5th edition (2007).

Classification:
*Family.*—Caryophyllaceae.
*Botanical.*—*Dianthus* x *allwoodii* hort.
*Designation.*—'KLEDA26818'.
*Type.*—Carnation.

Parentage:
*Female parent.*—*Dianthus* 'DSA-2024-3W503' (unpatented).

Plant:
*Propagation type.*—Vegetative stem cuttings.
*Time to produce a rooted young plant.*—28 days.
*Root description.*—Fine, color RHS 155A.
*Rooting habit shape.*—Lanceolate.
*Plant form.*—Upright, round.
*Plant height.*—11.0 cm to 14.0 cm.
*Plant diameter or spread.*—18.0 cm to 20.0 cm.

Lateral branches/stems:
*Shape of the branch in cross-section.*—Circular.
*Hollowness of the branch.*—Absent.

*Length.*—7.0 cm to 9.0 cm.
*Diameter.*—3.0 cm to 4.0 cm.
*Internode length.*—1.5 cm to 2.5 cm.
*Internode quantity per branch.*—3 to 4.
*Number of internodes per branch/stem.*—3 to 4.
*Node length.*—0.2 cm to 0.3 cm.
*Node diameter.*—0.2 cm.
*Texture.*—Smooth.
*Color.*—RHS 191A.
*Flower clustering on the lateral branch.*—None.

Foliage:
*Arrangement.*—Opposite.
*Length.*—3.0 cm to 5.0 cm.
*Width.*—0.4 cm.
*Shape.*—Linear.
*Apex.*—Narrowly acute.
*Base.*—Round.
*Margin.*—Entire.
*Texture* (*both upper and lower surfaces*).—Smooth.
*Cross-section of the leaf.*—Moderately concave.
*Curvature of the leaf.*—Absent.
*Glaucosity of the leaf.*—Weak, medium, or strong.
*Leaf color* (*both immature and mature*).—Immature: Upper surface: RHS 191A. Lower surface: RHS 191B. Mature: Upper surface: RHS 191A. Lower surface: RHS 191B.
*Venation pattern.*—Absent.

Flowers:
*Flower type and habit.*—Single and round.
*Fragrance.*—Present.
*Position of the flowers compared to the foliage of the plant.*—Moderately above.
*Profile of both the upper and lower part in the lateral view.*—Flat.
*Diameter of the flower.*—3.0 cm to 3.5 cm.
*Natural flowering season.*—Spring to autumn.
*Number of flowers per spray.*—3 to 4.
*Flower longevity on the plant.*—20 days.

Buds:
*Length.*—1 cm to 1.5 cm.
*Diameter.*—0.5 cm.
*Shape.*—Oblong.
*Color.*—Upper part: RHS 189A. Lower part: RHS 191A.
*Extrusion of the styles at the bud stage.*—Absent.

Corolla:
*Quantity of petals and arrangement.*—5 and arranged in one whorl.
*Corolla height.*—0.5 cm to 1 cm.
*Petal length.*—2.5 cm to 2.8 cm.
*Petal width.*—1.6 cm to 1.8 cm.
*Petal shape.*—Spoon shaped.
*Petal apex.*—Obtuse.
*Petal base.*—Acute.
*Petal margin.*—Inserted.
*Depth of petal margin.*—Shallow.
*Petal texture* (*both upper and lower surfaces*).—Smooth.
*Petal color.*—Immature: Upper surface: RHS 67B. Lower surface: RHS 75B. Mature: Upper surface: RHS 73A (macule) and RHS 73D margin. Lower surface: RHS 75C.
*Macule.*—Size: 0.5 cm to 0.7 cm. Color: RHS 73A.

Calyx:
*Quantity of sepals and arrangement.*—5.
*Longitudinal axis of the lobes of the calyx.*—Straight.
*Shape.*—Cylindric.
*Calyx height.*—1.2 cm to 1.4 cm.
*Calyx diameter* (*at the apex*).—0.5 cm.
*Sepal texture* (*both upper and lower surfaces*).—Smooth.
*Sepal color.*—Upper surface: RHS 189B. Lower surface: RHS 189C.
*Position of the outer lobes of the epicalyx in relation to the calyx.*—Adpressed.
*Apex shape of the outer lobes of the epicalyx.*—Acute, short acuminate, medium acuminate.
*Tip length of the outer lobes of the epicalyx.*—0.1 cm.
*Apex shape of the inner lobes of the epicalyx.*—Short acuminate.
*Tip length of the inner lobes of the epicalyx.*—0.1 cm.

Peduncles:
*Length.*—3.0 cm to 3.5 cm.
*Diameter.*—0.1 cm to 0.15 cm.
*Strength.*—Medium.
*Texture.*—Smooth.
*Color.*—RHS 191A.

Reproductive organs:
*Stamens.*—Quantity per flower: 6 to 8. Filament length: 0.5 cm to 0.7 cm. Filament color: RHS 155C. Anther length: 0.2 cm. Anther diameter: 0.1 cm. Anther color: RHS 158C. Pollen amount: Moderate.
*Pistils.*—Quantity per flower: 2. Length: 1.5 cm. Diameter: 0.1 cm. Stigma: Color: RHS 77B. Shape: Filamentous. Length: 0.2 cm. Diameter: 0.1 cm.
*Style.*—Color: RHS 75C. Length: 1.3 cm. Diameter: 0.1 cm.
*Ovary.*—Color: RHS 145B. Width: 0.4 cm.

Seeds: Absent.

Disease and insect resistance: No particular disease or insect resistance observed.

COMPARISON OF 'KLEDA26818' WITH PARENTAL LINE AND KNOWN VARIETY

'KLEDA26818' is distinguished from the parent as described in Table 1.

TABLE 1

Comparison with Parental Line

| Characteristic | 'KLEDA26818' | Female parent |
|---|---|---|
| Flower pattern | Maculated | Maculated and speckled |
| Macule width | Large | Small |

'KLEDA26818' can be compared to the commercial *Dianthus* variety 'WP19 NAM02' (unpatented). Differences between the varieties are described in Table 2.

TABLE 2

Comparison with Similar Variety

| Characteristic | 'KLEDA26818' | 'WP19 NAM02' (unpatented) |
|---|---|---|
| Flower color | Pink | Lavender-pink |
| Flower pattern | Maculated | Maculated and speckled |

I claim:

1. A new and distinct variety of *Dianthus* plant designated 'KLEDA26818' as illustrated and described herein.

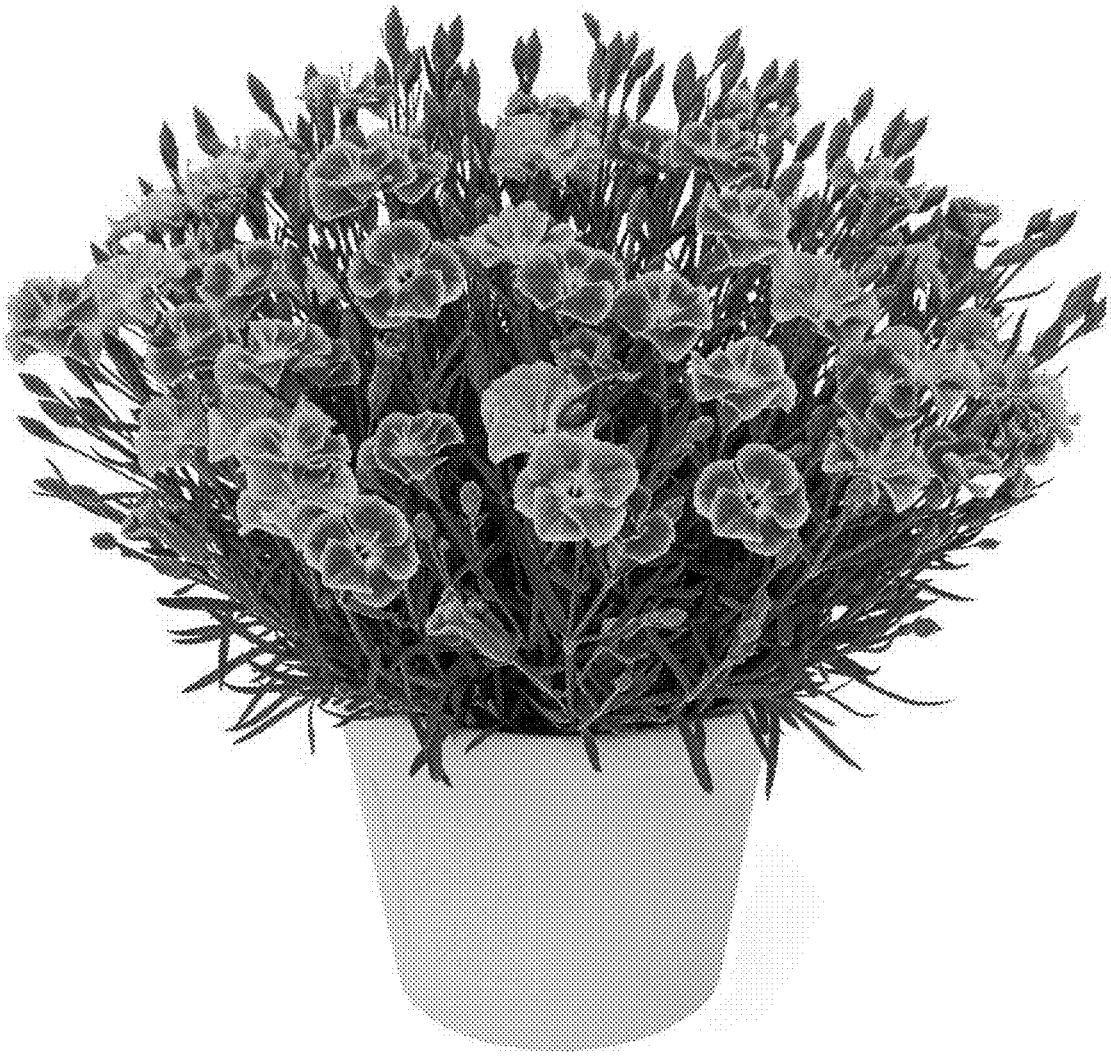

* * * * *